United States Patent [19]
Woehrl et al.

[11] Patent Number: 4,836,024
[45] Date of Patent: Jun. 6, 1989

[54] IMPACT SENSOR FOR MOTOR VEHICLES OR THE LIKE

[75] Inventors: Alfons Woehrl; Peter Hora, both of Schrobenhausen, Fed. Rep. of Germany

[73] Assignee: Messerschmitt-Boelkow Blohm GmbH, Munich, Fed. Rep. of Germany

[21] Appl. No.: 196,328

[22] Filed: May 20, 1988

[30] Foreign Application Priority Data

May 23, 1987 [DE] Fed. Rep. of Germany ....... 3717427

[51] Int. Cl.$^4$ ............................................. B60R 21/08
[52] U.S. Cl. ...................... 73/514; 280/735; 340/436; 307/10.1
[58] Field of Search ...................... 73/517 R; 180/274; 280/728, 734, 735, 806; 297/477, 478, 480; 307/10 R, 214; 340/52 H, 669

[56] References Cited

U.S. PATENT DOCUMENTS

| | | | |
|---|---|---|---|
| 3,870,894 | 3/1975 | Brede et al. | 340/52 H |
| 4,016,426 | 4/1977 | Nishioka | 340/52 H |
| 4,366,465 | 12/1982 | Venezieno | 340/52 H |
| 4,381,829 | 5/1983 | Montaron | 280/735 |
| 4,614,876 | 9/1986 | Mattes et al. | 340/52 H |
| 4,638,179 | 1/1987 | Mattes et al. | 280/735 |

FOREIGN PATENT DOCUMENTS

2207831 8/1973 Fed. Rep. of Germany.

Primary Examiner—Stewart J. Levy
Assistant Examiner—Robert P. Bell
Attorney, Agent, or Firm—W. G. Fasse; D. H. Kane, Jr.

[57] ABSTRACT

An impact sensor for detecting a collision of a motor vehicle or the like has at least two acceleration detectors, and a signal evaluating circuit for each detector for evaluating the output signals of the respective acceleration detectors. The evaluated signals are passed through a logic signal interpreting circuit to provide a control signal for triggering passive safety devices such as an inflatable air bag. In order to trigger the passive safety devices as quickly as possible in response to an impact or collision, and in order to determine the angular direction of the impact, several acceleration detectors having oriented sensitivity axes are provided, whereby the sensitivity axes of separate detectors are oriented in different directions. The signal evaluation and interpretation to provide the triggering signal make sure that only determined output signals of the acceleration detectors cause the intended triggering preferably only for frontal impact collisions.

10 Claims, 2 Drawing Sheets

IMPACT SENSOR FOR MOTOR VEHICLES OR THE LIKE

FIELD OF THE INVENTION

The invention relates to an impact sensor for sensing a collision of a motor vehicle or the like, including an acceleration detector arrangement and an evaluation circuit for generating a trigger signal for activating a passive safety device such as an inflatable air bag or a safety belt tensioning device if the output signal of the acceleration detector exceeds a certain critical threshold value.

DESCRIPTION OF THE PRIOR ART

An impact sensor of the above described general type for triggering a passive safety system for protecting the occupants or passengers of a motor vehicle, is known from the German Patent Publication (DE-OS) No. 2,207,831 disclosing an impact sensor including an acceleration detector, for example, a piezoelectric crystal of which the sensitivity axis is arranged in an essentially horizontal plane oriented in the driving direction. The output signals of the piezoelectric crystal are supplied to an evaluation circuit in which the output signals undergo a threshold evaluation and are then essentially integrated once or twice. A trigger signal is generated to activate the passive safety system in the event of an impact or collision accident of the motor vehicle if the evaluated signal exceeds a certain threshold value corresponding to a critical velocity in the case of a single integration or a critical path distance in the event of a double integration. The passive safety system, for example, includes an inflatable air bag or a safety belt tensioning device for tensioning or pulling taut the safety belts for the occupants or passengers of the motor vehicle.

In addition to using safety systems, modern motor vehicles are also provided with so-called active safety devices. Such active safety systems are achieved especially in that the vehicle chassis or frame includes so-called crumple- or crush-zones which uniformly deform to a prescribed extent in the event of an impact or collision accident of the motor vehicle and thereby absorb a large portion of the impact energy. However, because of the structural arrangement of the crush zones the risk now arises that the output signals delivered by the acceleration detector react late, so to speak, or include a certain time delay. Thus, the passive safety device system may correspondingly be activated too late. It would be desirable to develope an impact sensor which assures that the active and passive safety systems cooperate in an optimal manner.

OBJECTS OF THE INVENTION

In view of the foregoing it is the aim of the invention to achieve the following objects singly or in combination:

to provide an impact sensor and evaluation system of the above described general type which may easily be adapted to cooperate with the specific structural arrangement of crumple- or crush-zones of individual motor vehicles;

to assure the proper and timely activation of passive safety devices in a motor vehicle employing such an impact sensor and evaluation system;

to construct an impact sensor system capable of distinguishing between a front impact and a rear impact under all possible driving angle conditions;

to orient an impact sensor at an angle away from the driving direction of the motor vehicle to improve the response characteristic; and to arrange at least two impact sensors oriented at angles away from the driving direction in order to achieve an accurate determination of the impact direction so that appropriate safety devices may be activated.

SUMMARY OF THE INVENTION

The above objects have been achieved in an impact sensor for motor vehicles according to the invention, wherein an impact sensor in the motor vehicle or the like includes at least two acceleration detectors each having an oriented sensitivity axis, or axis of greatest sensitivity. The sensitivity axis of each detector points in a different direction. The orientation of these sensitivity axes may, for example, be such that the axes are at an angle with respect to one another or with respect to the travel direction dependent upon the structural arrangement of the crumple-zones of the vehicle. An output of each acceleration detector is connected to an input of its own separate, dedicated signal evaluating circuit or channel leading to a signal validating or interpreting circuit for processing the output signal of each acceleration detector to form a control signal at the output of the signal validating or interpreting circuit for activating safety means in accordance with the results of the signal evaluation and validation. The control signal is provided by the signal validating circuit as a trigger signal for passive safety devices only if the output signal of at least one evaluating circuit or channel islarger than a first large threshold signal value and simultaneously the output signal of at least one other evaluating circuit or channel is larger than a second small threshold signal value. Preferably, the sensitivity axis of one detector is oriented in a direction having an opposite sign compared to the sensitivity axis direction of the other detector relative to the travel or driving direction of the motor vehicle. Preferably, the amplitudes of the detected signal are interpreted relative to respective threshold signal values.

According to the arrangement of the invention,the specific angular orientation of the respective motor vehicle or the like, in an impact or collision accident may be determined and taken into consideration. Thus, it is possible to distinguish between a front collision impact and a rear collision impact under all possible driving angle conditions. Preferably, the detectors are installed in the motor vehicle in such a manner that their respective sensitivity axes are oriented at an acute angle relative to the driving direction of the motor vehicle. The angles between the respective sensitivity axis and the driving direction may be the same or may be different. It has been shown to be advantgeous in many instances to use two acceleration detectors of which the sensitivity axes are oriented at +30° and −30° respectively relative to the driving direction. Other arrangements, for example, with sensitivity areas oriented at +30° and −45° are also possible and may be particularly advantageous for special structural arrangements of the crumpling-or crush-zones and the like of the motor vehicle.

The signal processing in the impact sensor according to the invention may be carried out in an analog manner, in a digital manner, or with a combination of analog and digital stages.

The validation of the output signals of the acceleration detectors may be carried out in a simple manner by means of differential amplifier stages in the signal processing channels in which the output signals are compared with threshold values. Such a threshold value may, for example, be a minimum critical velocity value. As soon as this threshold value is reached or exceeded in a first processing channel and a second smaller reference or threshold value is similarly exceeded in a second channel, then an output control signal is generated. By means of this signal combining processing it is ensured that both signal processing channels must exceed a reference of threshold value before the chanel having the larger signal amplitude generates the output signal for controlling or triggering a safety device.

In the case of a rear impact collision neither one of the two signal processing channels exceeds the reference value and in the case of a side impact collision only one of the two signal processing channels exceeds the reference value so that no output signal is generated in these cases.

Contrary to the findings of prior experimets, it has been determined according to the invention that it is not necessary to orient an acceleration detector with its sensitivity axis aligned with the travel direction of the motor vehicle or the like. Rather, in order to achieve the timely triggering and activation of the passive safety devices, it is advantageous to deviate from the prior teaching and actually orient the sensitivity axes of the acceleration detectors at an angle which is more or less acute relative to the driving direction of the motor vehicle. Depending upon various conditions, the respective acute angles may be larger or smaller.

With this arrangement of the acceleration detectors according to the invention, an evaluation of the signals may be carried out with consideration of the sensitivity characteristics of two acceleration detectors, so that a clear and unambiguous determination of the direction of an impact in the plane of the detectors is possible.

Triggering of the safety devices in reponse to rear impact collisions over an angular range of 180°±90° relative to the forward travel direction is suppressed because the comparators of the separate channels are coupled by a signal interpreting logic state. This is achieved in that the comparator of at least one processing channel provides a low signal in response to a side impact, while both channels provide a low signal in response to a rear impact. The low signal is delivered to an AND-gate of the opposite processing channel. Thus, the throughput of the signals from second comparators of each processing channel is suppressed.

BRIEF DESCRIPTION OF THE DRAWINGS

In order that the invention may be clearly understood, it will now be described, by way of example, with reference to the accompanying drawings, wherein.

DETAILED DESCRIPTION OF PREFERRED EXAMPLE EMBODIMENTS AND OF THE BEST MODE OF THE INVENTION

Figure 1:
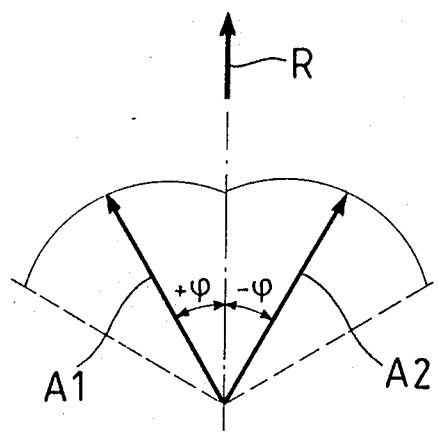
FIG. 1 shows schematically the direction of orientation of the sensitivity axes of two impact acceleration detectors relative to a travel direction of a motor vehicle.

FIG. 1 shows a sensitivity axis A1 of a first acceleration detector and a sensitivity axis A2 of a second acceleration detector. The first sensitivity axis A1 is oriented at an angle $+\rho$ relative to the forward travel direction R of a motor vehicle, and the second sensitivity axis A2 is oriented at an angle $-\rho$ relative to the forward to the travel direction R. In FIG. 1, for example, the angle $\rho$ corresponds to 30°. The sensitivity of the associated respective acceleration detectors has a cosine $\rho$ characteristic about the respective axis A1 or A2 as indicated by the curved arcs arranged symmetrically about the axes A1 and A2. Thus, the sensitivity of each detector is greatest in the direcion of its sensitivity axis and tapers off as a cosine function at any angle away from the respective axis.

Figure 2:
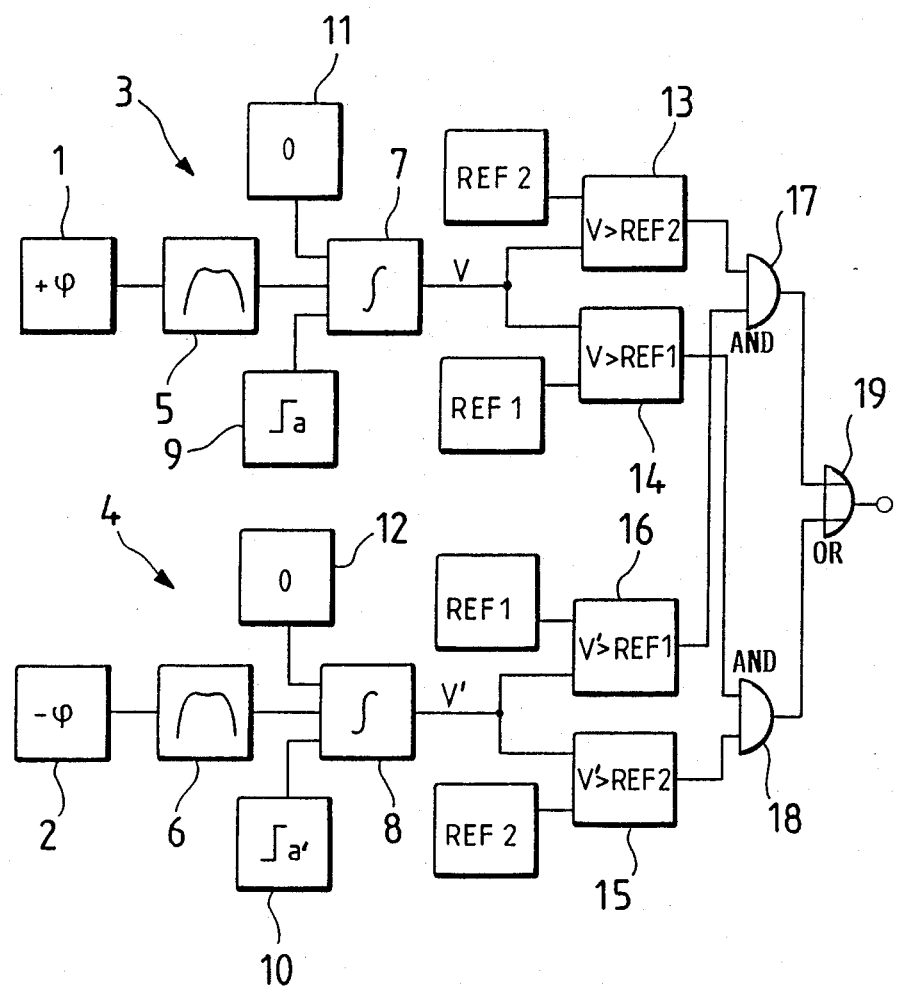
FIG. 2 is a block circuit diagram of a first embodiment of an impact sensor according to the invention having two acceleration detectors oriented according to FIG. 1.

FIG. 2 shows a circuit diagram for an impact sensor having two acceleration detectors 1 and 2 oriented with their sensitivity axes A1 and A2 directed as shown in FIG. 1 at angles of $+\rho$ and $-\rho$ relative to the forward travel direction. The output signals of the acceleration detectors 1 and 2 are applied to two equally constructed signal processing channels 3 and 4 respectively. The output signal of each acceleration detector 1 or 2 is first applied to a prefilter stage 5 or 6 respectively and then applied to an integrator 7 or 8 respectively. A threshold circuit 9 or 10 is provided for each integrator 7 or 8 respectively for determining or setting a threshold value a or a' respectively above which the signal output from the prefilter stages or signal forming stages 5 or 6 respectively is integrated. Furthermore, a null point adjuster 11 or 12 is provided for each integrator 7 or 8 respectively. Because the signal output by each prefilter or signal forming stage 5 or 6 is dependent upon the acceleration or deceleration which is effective on the corresponding acceleration detector 1 or 2, the output signal of the integrator 7 or 8 is a velocity dependent signal V or V' respectively.

The velocity dependent signal V is applied as an input to two comparators 13 and 14 while the velocity dependent signal V' is applied as an input to two comparators 15 and 16. A first reference value REF1 is applied as a second input to the comparator 14 and to the comparator 16. A second reference value REF2 is applied as a second input to the comparator 13 and to the comparator 15. The reference or threshold value REF2 is larger than the threshold value REF1. The reference or threshold values REF1 and REF2 correspond to critical velocities at which the passive safety devices, for example, air bags, should be triggered or inflated. These values are determined as experimental values and may be different for different vehicle types. Thus, in each signal processing channel 3 or 4, the voltage dependent signal V or V' respectively is compared to both a larger threshold value REF2 and a smaller threshold value REF1. The output signal of the comparator 13 of the first signal processing channel 3 for the acceleration detector 1, and the output signal of the comparator 16 of the second signal processing channel 4 for the acceleration detector 2 are supplied as the two inputs to an AND-gate 17. Correspondingly, the outputs of the comparators 14 and 15 are supplied at the two inputs to a second AND-gate 18. In this manner the two signal processing channels 3 and 4 are cross-coupled in a signal validating circuit including both AND-gates 17 and 18 and an OR-gate 19. The outputs of the AND-gates are supplied as the two inputs to the OR-gate 19 of which the output is used as a control signal for a triggering circuit (not shown) for the passive safety devices.

In the above described case, by means of coupling the comparators 13 to 16 through the AND-gates 17 and 18, the passive safety devices are triggered or activated dependent upon the signals output by the acceleration detectors. As a result of the arrangement of the sensitivity axes of the acceleration detectors 1 and 2, and due to the above described circuit coupling, the passive safety devices are only activated for frontal impact collisions over the angular range of 0° to ±90° from the forward travel direction. Furthermore, the safety devices are activated at the earliest possible time, whereby the greatest possible safety for the passengers or occupants of the vehicle is achieved.

Figure 3:
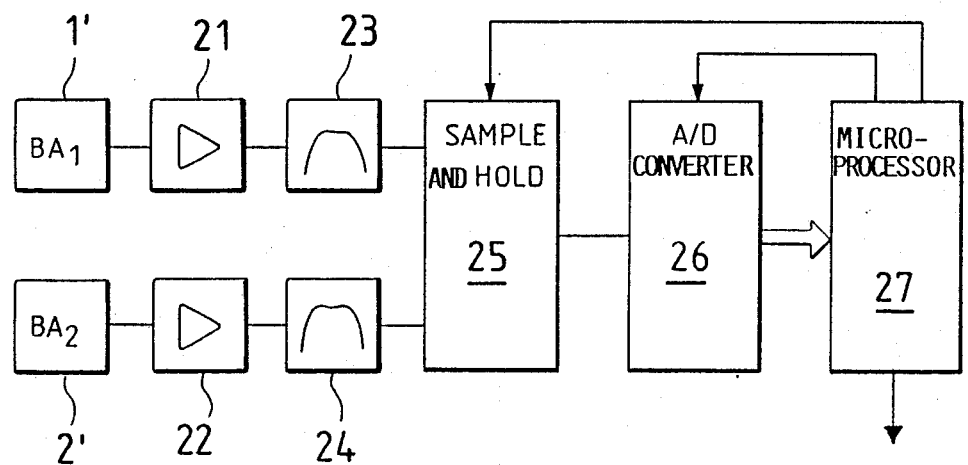
FIG. 3 is a block circuit diagram of a second embodiment of an impact sensor according to the invention, including digital processing stages and having two acceleration detectors oriented according to FIG. 1.

FIG. 3 shows a second embodiment of an impact sensor according to the invention, similarly having two acceleration detectors 1' and 2' having directional sensitivities BA1 and BA2, respectively. The acceleration sensors 1' and 2' are arranged in the motor vehicle with their respective sensitivity axes A1 and A2 oriented according to FIG. 1. The output signal of each acceleration detector 1' or 2' is applied as an input to a preamplifier 21 or 22 respectively, of which the output is applied to a prefilter stage 23 or 24 respectively. The output signals of both prefilters 23 and 24 are input into a sample and hold circuit 25 where they are stored. Then the output of the sample and hold circuit 25 is supplied to an analog-to-digital converter 26. The digital output signals of the A/D converter 26 are applied to a microprocessor 27 where they are processed. The microprocessor 27 simultaneously controls the function of the sample and hold circuit 25 and the analog-to-digital converter 26. The signal processing which is carried out in the microprocessor 27 is similar to that shown in FIG. 2 for analog processing elements, but is carried out in a digital manner. Circuits 25, 26, and 27 are conventional.

Although the invention has been described with reference to specific example embodiments, it will be appreciated, that it is intended to cover all modifications and equivalents within the scope of the appended claims.

What we claim is:

1. An impact sensor, especially for sensing a collision of a motor vehicle or the like travelling in a forward driving direction (R), comprising a plurality of acceleration detectors each having a sensitivity axis oriented in a different direction and each generating an output signal in response to an impact, a separate signal evaluating circuit means connected to each detector for individually evaluating each of said output signals to determine whether it exceeds a preliminary threshold value (a, a') and then to generate an evaluated output signal (V, V'), means for providing a first threshold value and means for providing a second threshold value, whereby said first threshold value is larger than said second threshold value, and signal validating means connected to said signal evaluating means for generating a control signal for activating passive safety devices if an evaluated output signal generated by at least one of said signal evaluating circuit means is larger than said first threshold value and simultaneously a further evaluated output signal generated by another signal evaluating circuit means is larger than said second threshold value.

2. The impact sensor of claim 1, wherein each of said acceleration detectors is arranged so that the respective sensitivity axis forms an acute angle ($\rho$) relative to said forward driving direction (R).

3. The impact sensor of claim 1, wherein said plurality of acceleration detectors comprises two acceleration detectors.

4. The impact sensor of claim 1, wherein said sensitivity axes are arranged in a common plane with said forward driving direction.

5. The impact sensor of claim 1, wherein said sensitivity axes are arranged as at least one pair of sensitivity axes arranged on opposite sides of said forward driving direction with angles of equal magnitude relative to said forward driving direction.

6. The impact sensor of claim 1, wherein each of said signal evaluating circuit means comprises integrator circuit means (7, 8), said signal validating means comprise comparator means (13 to 16) connected to said integrator circuit means and to said means for providing a first and a second threshold value for comparing each said evaluated output signal with said first and second threshold values, and wherein said signal validating circuit means further comprise logic coupling circuit means interconnecting the outputs of said comparator means (13 to 16) for providing said control signal.

7. The impact sensor of claim 1, wherein said first and second threshold values are voltage amplitude threshold values, and said output signals and said evaluated output signals are voltage amplitude signals.

8. The impact sensor of claim 1, wherein at least said signal validating circuit means form part of a microprocessor (27).

9. The impact sensor of claim 1, wherein said sensitivity axes are not arranged in a common plane with said forward driving direction.

10. The impact sensor of claim 8, further comprising sample and hold circuit means and analog-to-digital converter means connected between said separate signal evaluating circuit means and said microprocessor.

* * * * *